(12) United States Patent
Zadno-Azizi et al.

(10) Patent No.: US 7,033,387 B2
(45) Date of Patent: Apr. 25, 2006

(54) BODY FLUID FLOW CONTROL DEVICE

(75) Inventors: Gholam-Reza Zadno-Azizi, Newark, CA (US); John S. Ford, Manhattan Beach, CA (US); April Marano-Ford, Manhattan Beach, CA (US)

(73) Assignee: Emphasys Medical, Inc., Redwood city, CA (US)

( * ) Notice: Subject to any disclaimer, the term of this patent is extended or adjusted under 35 U.S.C. 154(b) by 0 days.

(21) Appl. No.: 10/419,653

(22) Filed: Apr. 18, 2003

(65) Prior Publication Data

US 2003/0199972 A1 Oct. 23, 2003

Related U.S. Application Data

(63) Continuation of application No. 09/397,218, filed on Sep. 16, 1999, now Pat. No. 6,632,243, which is a continuation of application No. 08/931,552, filed on Sep. 16, 1997, now Pat. No. 5,954,766.

(51) Int. Cl.
*A61F 2/06* (2006.01)
(52) U.S. Cl. ............... 623/1.24; 623/23.68; 623/23.7; 606/191; 600/29
(58) Field of Classification Search ............ 623/1.1, 623/1.2, 1.11–1.13, 1.23–1.26, 1.18–1.19, 623/2.14, 2.18, 2.17, 2.28, 900, 12, 11.11, 623/66.1, 1.32–1.33, 23.64–23.71, 9; 128/898; 606/191–200; 600/29–32, 36
See application file for complete search history.

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,667,069 A | 6/1972 | Blackshear et al. | 623/3.1 |
| 3,788,327 A | 1/1974 | Donowitz et al. | 128/350 |

(Continued)

FOREIGN PATENT DOCUMENTS

EP 0621 015 (A1) 10/1994

(Continued)

OTHER PUBLICATIONS

Al Jishi et al., "Selective Bronchial Occlusion for Treatment of Bullous Interstitial Emphysema and Bronchopleural Fistula." *J. of Pediatric Surgery,* 29:1545-1547, 1994.

(Continued)

*Primary Examiner*—David J. Isabella
*Assistant Examiner*—Urmi Chattopadhyay
(74) *Attorney, Agent, or Firm*—Fish & Richardson P.C.; Fred C. Hernandez

(57) ABSTRACT

A device to provide body fluid flow control in the form of a valve to be located within a duct or passageway. The device is controlled through pressure above a preselected threshold. Bulk resilience about a passageway in a valve body provides the mechanism for controlled flow. One-way valve operation may be provided through a flap or through a pressure differential on the valve body depending upon the direction of flow. A frame structure positioned within a resilient seal includes longitudinally elongate elements which may be of spring material, malleable material or heat recoverable material so as to accomplish an initial insertion state and an expanded anchoring state. A valve support transitions between the resilient seal portion and the valve body to insure that the states do not change the threshold opening pressure. Insertion devices may be employed to position and actuate a change of state of the frame in the body duct or passageway.

18 Claims, 6 Drawing Sheets

U.S. PATENT DOCUMENTS

| | | | |
|---|---|---|---|
| 3,874,388 A | 4/1975 | King et al. ............... 128/334 |
| 4,014,318 A | 3/1977 | Dockum et al. ............... 128/1 |
| 4,086,665 A | 5/1978 | Poirier ............... 623/1 |
| 4,212,463 A | 7/1980 | Repinski et al. ............ 273/418 |
| 4,250,873 A | 2/1981 | Bonnet ............... 600/104 |
| 4,302,854 A | 12/1981 | Runge ............... 3/1.7 |
| 4,477,930 A | 10/1984 | Totten et al. ............... 3/1.5 |
| 4,710,192 A | 12/1987 | Liotta et al. ............... 623/1 |
| 4,732,152 A | 3/1988 | Wallsten et al. ............ 128/343 |
| 4,759,758 A | 7/1988 | Gabbay ............... 623/2 |
| 4,795,449 A | 1/1989 | Schneider et al. ........... 604/329 |
| 4,808,183 A | 2/1989 | Panje ............... 623/9 |
| 4,819,664 A | 4/1989 | Nazari ............... 128/207.15 |
| 4,830,003 A | 5/1989 | Wolff et al. ............... 128/343 |
| 4,832,680 A | 5/1989 | Haber et al. ............... 600/31 |
| 4,846,836 A | 7/1989 | Reich ............... 623/11 |
| 4,850,999 A | 7/1989 | Planck ............... 623/1 |
| 4,852,568 A | 8/1989 | Kensey ............... 128/325 |
| 4,877,025 A | 10/1989 | Hanson ............... 128/107.16 |
| 4,934,999 A | 6/1990 | Bader ............... 600/29 |
| 4,968,294 A | 11/1990 | Salama ............... 600/30 |
| 5,061,274 A | 10/1991 | Kensey ............... 606/213 |
| 5,116,360 A | 5/1992 | Pinchuk et al. ............... 623/1 |
| 5,116,564 A | 5/1992 | Jansen et al. ............... 264/255 |
| 5,123,919 A | 6/1992 | Sauter et al. ............... 623/2 |
| 5,151,105 A | 9/1992 | Kwan-Gett ............... 623/1 |
| 5,161,524 A | 11/1992 | Evans ............... 128/203.15 |
| 5,306,234 A | 4/1994 | Johnson ............... 604/49 |
| 5,352,240 A | 10/1994 | Ross ............... 623/2 |
| 5,358,518 A | 10/1994 | Camilli ............... 623/2 |
| 5,366,478 A | 11/1994 | Brinkerhoff et al. ........ 660/213 |
| 5,382,261 A | 1/1995 | Palmaz ............... 606/158 |
| 5,392,775 A | 2/1995 | Adkins et al. .......... 128/207.16 |
| 5,409,019 A | 4/1995 | Wilk ............... 128/898 |
| 5,411,507 A | 5/1995 | Heckele ............... 606/108 |
| 5,411,552 A | 5/1995 | Andersen et al. ............... 623/2 |
| 5,413,599 A | 5/1995 | Imachi et al. ............... 623/2 |
| 5,417,226 A | 5/1995 | Juma ............... 128/885 |
| 5,445,626 A | 8/1995 | Gigante ............... 604/349 |
| 5,486,154 A | 1/1996 | Kelleher ............... 600/104 |
| 5,499,995 A | 3/1996 | Teirstein ............... 606/192 |
| 5,500,014 A | 3/1996 | Quijano et al. ............... 623/2 |
| 5,562,608 A | 10/1996 | Sekins et al. ............... 604/20 |
| 5,645,565 A | 7/1997 | Rudd et al. ............... 606/213 |
| 5,660,175 A | 8/1997 | Dayal ............... 128/207.15 |
| 5,662,713 A | 9/1997 | Andersen et al. ............... 623/12 |
| 5,683,451 A | 11/1997 | Lenker et al. ............... 623/1 |
| 5,697,968 A | 12/1997 | Rogers et al. ............... 623/1 |
| 5,755,770 A | 5/1998 | Ravenscroft ............... 623/1 |
| 5,782,916 A * | 7/1998 | Pintauro et al. ........ 623/23.66 |
| 5,800,339 A | 9/1998 | Salama ............... 600/29 |
| 5,824,037 A | 10/1998 | Fogarty et al. ............... 623/1.13 |
| 5,840,081 A | 11/1998 | Andersen et al. ............... 623/2 |
| 5,843,158 A | 12/1998 | Lenker et al. ............... 623/1.13 |
| 5,851,232 A | 12/1998 | Lois ............... 623/1 |
| 5,855,587 A | 1/1999 | Hyon et al. ............... 606/188 |
| 5,855,597 A | 1/1999 | Jayaraman ............... 623/1 |
| 5,855,601 A | 1/1999 | Bessler et al. ............... 623/2 |
| 5,868,779 A | 2/1999 | Ruiz ............... 606/194 |
| 5,891,195 A * | 4/1999 | Klostermeyer et al. .... 623/1.26 |
| 5,893,826 A * | 4/1999 | Salama ............... 600/31 |
| 5,944,738 A | 8/1999 | Amplatz et al. ............... 606/213 |
| 5,947,997 A | 9/1999 | Pavcnik et al. ............... 606/213 |
| 5,954,765 A | 9/1999 | Ruiz ............... 623/1.15 |
| 5,954,766 A | 9/1999 | Zadno-Azizi et al. ........... 623/2 |
| 5,957,949 A | 9/1999 | Leonhardt et al. ............... 606/194 |
| 5,976,174 A | 11/1999 | Ruiz ............... 606/213 |
| 5,984,965 A | 11/1999 | Knapp et al. ............... 623/12 |
| 5,989,288 A * | 11/1999 | Pintauro et al. ............... 600/30 |
| 6,007,575 A | 12/1999 | Samuels ............... 623/1 |
| 6,009,614 A | 1/2000 | Morales ............... 29/516 |
| 6,020,380 A | 2/2000 | Killian ............... 514/570 |
| 6,022,312 A | 2/2000 | Chaussy et al. ............... 600/29 |
| 6,027,525 A | 2/2000 | Suh et al. ............... 623/1 |
| 6,051,022 A | 4/2000 | Cai et al. ............... 623/2 |
| 6,068,635 A | 5/2000 | Gianotti ............... 606/108 |
| 6,068,638 A | 5/2000 | Makower ............... 606/159 |
| 6,077,291 A | 6/2000 | Das ............... 606/213 |
| 6,083,255 A | 7/2000 | Laufer et al. ............... 607/96 |
| 6,123,663 A | 9/2000 | Rebuffat |
| 6,135,729 A | 10/2000 | Aber ............... 417/420 |
| 6,135,991 A | 10/2000 | Muni et al. ............... 604/509 |
| 6,141,855 A | 11/2000 | Morales ............... 29/516 |
| 6,162,245 A | 12/2000 | Jayaraman ............... 623/1.15 |
| 6,168,614 B1 | 1/2001 | Andersen et al. ............... 623/1 |
| 6,174,323 B1 | 1/2001 | Biggs et al. ............... 606/232 |
| 6,183,520 B1 | 2/2001 | Pintauro et al. ......... 623/23.64 |
| 6,200,333 B1 | 3/2001 | Laufer ............... 607/96 |
| 6,206,918 B1 | 3/2001 | Campbell et al. ........... 623/2.32 |
| 6,234,996 B1 | 5/2001 | Bagaoisan et al. ........ 604/97.01 |
| 6,240,615 B1 | 6/2001 | Kimes et al. ............... 29/516 |
| 6,245,102 B1 | 6/2001 | Jayaraman ............... 623/1.15 |
| 6,258,100 B1 | 7/2001 | Alferness et al. ............... 606/108 |
| 6,270,527 B1 | 8/2001 | Campbell et al. ............... 623/2.18 |
| 6,287,290 B1 | 9/2001 | Perkins et al. ............... 604/516 |
| 6,293,951 B1 | 9/2001 | Alferness et al. ............... 606/108 |
| 6,302,893 B1 | 10/2001 | Limon et al. ............... 606/108 |
| 6,312,407 B1 | 11/2001 | Zadno-Azizi et al. .. 604/103.03 |
| 6,325,777 B1 | 12/2001 | Zadno-Azizi et al. .... 604/97.01 |
| 6,325,778 B1 | 12/2001 | Zadno-Azizi et al. .... 604/99.02 |
| 6,327,772 B1 | 12/2001 | Zadno-Azizi et al. ......... 29/557 |
| 6,328,689 B1 | 12/2001 | Gonzalez et al. ............... 600/37 |
| 6,355,014 B1 | 3/2002 | Zadno-Azizi et al. .... 604/99.02 |
| 6,398,775 B1 | 6/2002 | Perkins et al. ............... 604/514 |
| 6,402,754 B1 | 6/2002 | Gonzalez ............... 606/69 |
| 6,416,554 B1 | 7/2002 | Alferness et al. ........ 623/23.65 |
| 6,458,076 B1 | 10/2002 | Pruitt ............... 600/146 |
| 6,485,407 B1 | 11/2002 | Alferness et al. ............... 600/37 |
| 6,491,706 B1 | 12/2002 | Alferness et al. ............... 606/157 |
| 6,493,589 B1 | 12/2002 | Medhkour et al. ............. 607/99 |
| 6,510,846 B1 | 1/2003 | O'Rourke ............... 128/200.21 |
| 6,527,761 B1 | 3/2003 | Buch et al. ............... 604/516 |
| 6,632,243 B1 | 10/2003 | Zadno-Azizi et al. ...... 623/1.24 |
| 2001/0025132 A1 | 9/2001 | Alferness et al. ............... 600/37 |
| 2001/0037808 A1 | 11/2001 | Deem et al. ............ 128/200.24 |
| 2001/0041906 A1 | 11/2001 | Gonzalez ............... 606/191 |
| 2001/0051799 A1 | 12/2001 | Ingenito ............... 604/516 |
| 2001/0052344 A1 | 12/2001 | Doshi ............... 128/207 |
| 2001/0056274 A1 | 12/2001 | Perkins et al. ............... 604/516 |
| 2002/0007831 A1 | 1/2002 | Davenport et al. .... 128/200.24 |
| 2002/0062120 A1 | 5/2002 | Perkins et al. ............... 604/516 |
| 2002/0077593 A1 | 6/2002 | Perkins et al. ........... 604/96.01 |
| 2002/0077696 A1 | 6/2002 | Zadno-Azizi et al. ...... 623/1.24 |
| 2002/0087153 A1 | 7/2002 | Roschak et al. ............... 606/27 |
| 2002/0095209 A1 | 7/2002 | Zadno-Azizi et al. ...... 623/1.24 |
| 2002/0111619 A1 | 8/2002 | Keast et al. ............... 606/41 |
| 2002/0111620 A1 | 8/2002 | Cooper et al. ............... 606/41 |
| 2002/0112729 A1 | 8/2002 | DeVore et al. ......... 128/207.15 |
| 2002/0138135 A1 | 9/2002 | Duerig et al. ............... 623/1.24 |
| 2003/0018327 A1 | 1/2003 | Truckai et al. ............... 606/32 |
| 2003/0018344 A1 | 1/2003 | Kaji et al. ............... 606/130 |
| 2003/0050648 A1 | 3/2003 | Alferness et al. ............ 606/108 |
| 2003/0083671 A1 | 5/2003 | Rimbaugh et al. ............ 606/108 |
| 2003/0212452 A1 | 11/2003 | Zadno-Azizi et al. ...... 623/1.24 |

FOREIGN PATENT DOCUMENTS

| | | |
|---|---|---|
| EP | 0621 015 (B1) | 10/1994 |
| EP | 1 078 601 (A2) | 2/2001 |
| EP | 01/28433 (A1) | 4/2001 |
| EP | 1 151 729 (A1) | 11/2001 |
| GB | 2324729 | 4/1998 |
| RU | 2140211 | 10/1999 |
| SU | 852321 | 7/1981 |

| | | |
|---|---|---|
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 (A1) | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 (A1) | 12/1999 |
| WO | 00/15149 | 3/2000 |
| WO | 00/42950 | 7/2000 |
| WO | 00/51510 | 9/2000 |
| WO | 00/62699 | 10/2000 |
| WO | 00/78386 (A1) | 12/2000 |
| WO | 00/78407 (A1) | 12/2000 |
| WO | 01/02042 (A1) | 1/2001 |
| WO | 01/03642 (A1) | 1/2001 |
| WO | 01/05334 (A1) | 1/2001 |
| WO | 01/10313 (A1) | 2/2001 |
| WO | 01/10314 (A2) | 2/2001 |
| WO | 01/12104 (A1) | 2/2001 |
| WO | 01/13839 (A1) | 3/2001 |
| WO | 01/13908 (A2) | 3/2001 |
| WO | 01/45590 (A2) | 6/2001 |
| WO | 01/49213 (A2) | 7/2001 |
| WO | 01/54585 (A1) | 8/2001 |
| WO | 01/54625 (A1) | 8/2001 |
| WO | 01/54685 (A1) | 8/2001 |
| WO | 01/66190 (A2) | 9/2001 |
| WO | 01/74271 (A1) | 10/2001 |
| WO | 01/87170 (A1) | 11/2001 |
| WO | 01/89366 (A2) | 11/2001 |
| WO | 01/95786 (A2) | 12/2001 |
| WO | 02/05884 (A2) | 1/2002 |
| WO | 02/22072 (A2) | 3/2002 |
| WO | 02/32333 (A1) | 4/2002 |
| WO | 02/34322 (A2) | 5/2002 |
| WO | 02/38038 (A2) | 5/2002 |
| WO | 02/47575 (A2) | 6/2002 |
| WO | 02/056794 (A2) | 7/2002 |
| WO | 02/064045 (A1) | 8/2002 |
| WO | 02/064190 (A2) | 8/2002 |
| WO | 02/064190 (A3) | 8/2002 |
| WO | 02/069823 (A2) | 9/2002 |
| WO | 02/069823 (A3) | 9/2002 |
| WO | 02/094087 (A1) | 11/2002 |
| WO | 03/022124 (A2) | 3/2003 |

OTHER PUBLICATIONS

Article: "Autocath® 100—Nonsurgical, Intraurethral Bladder Control Device for Incontinent and Retentive Women—Dr. Kulisz's Development".

Derwent citing Russian Patent No. RU 2140211, published Oct. 27, 1999, for : "Method of surgical treatment of patients with pathology of respiratory organs complicated with pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc No.: 1988-241181/198834 (citing Russian Application No. SU4026409, published Feb. 21, 1986), Russian Patent No. SU 1371700.

Derwent# 008650867 WPI Acc No.: 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919.

Lewis et al., "Pulmonary Interstitial Emphysema: Selective Broncial Occlusion with a Swan-Ganz Catheter", *Archives of Disease in Childhood, 63*:313-315, 1988.

Mathew et al., "Selective bronchial obstruction for treatment of bullous interstitial emphysema." *J. of Ped., 96*:475-477, 1980.

Okada et al., "Emergent Bronchofiberoptic Bronchial Occlusion for Intractable Pneumothorax with Severe Emphysema", *The Jap. J. of Thor. and Cardio. Sur., 46*:1078-1081, 1998.

Puhakka et al., "Acute Bronchial Obstruction: An Experimental Rabbit Model Study." *Int. J. of Pediatric Otorhinolaryngology, 18*:107-118, 1989.

Snider et al., *The Definition of Emphysema*: Report of the National Heart Lung and Blood Institute, Division of Lung Diseases Workshop, *Am. Rev. Respir. Dis., 132*:182-185, 1985.

Woodring et al., "Pneumothorax Vacuo", *CHEST, 100*:1102-1124, 1996.

\* cited by examiner

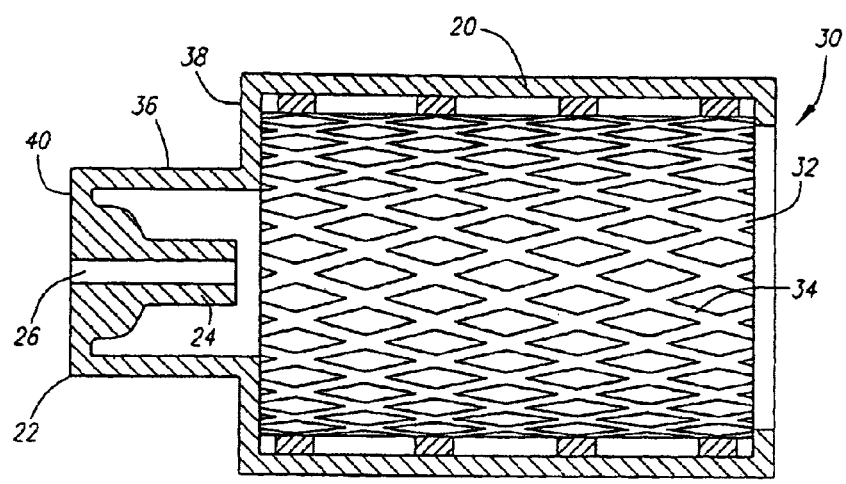
FIG. 3
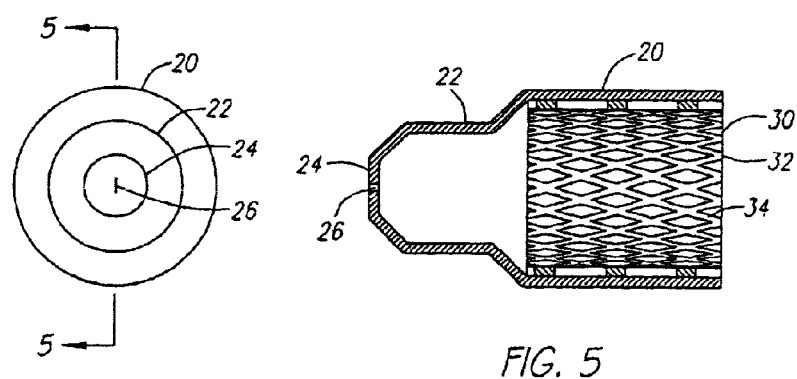
FIG. 4
FIG. 5

BODY FLUID FLOW CONTROL DEVICE

CROSS-REFERENCE TO RELATED APPLICATIONS

This application is a continuation of U.S. patent application Ser. No. 09/397,218 entitled "Body Fluid Flow Control Device", filed Sep. 16, 1999 and issuing as U.S. Pat. No. 6,632,243, which is a continuation of U.S. patent application Ser. No. 08/931,552, filed Sep. 16, 1997 and issuing as U.S. Pat. No. 5,954,766, the full disclosures of which are incorporated herein by reference.

BACKGROUND OF THE INVENTION

The field of the present invention is valve mechanisms for use in the human body.

Valves play an important role in a number of bodily functions. One such physiologic valve is in the urinary tract. Valve failure in this system leads to urinary incontinence, a significant health issue. Urinary incontinence is estimated to affect some ten million Americans. The full extent of this problem is unknown because less than half of affected adults are believed to actually seek medical attention.

Devices are available to assist in the control of urinary incontinence. Such devices include external valves, valves extending throughout the lower urinary tract and into the bladder, devices extending through long portions of the urethra and implanted prostheses as well as injected bulking agents which support the urethral sphincter to enhance operation. Such devices are often inconvenient, uncomfortable and/or require surgical insertion. Other devices are considered overly intrusive.

Native valves are also found in cardiovascular systems. In veins, native venous valves promote one-way flow toward the heart from the periphery. Diseases exist such as venous thrombosis and thrombophlebitis which can render native venous valves incompetent, resulting in edema. Replacement of these native valves with artificial ones could provide substantial health benefits.

The pulmonic valve associated with the heart is yet another native flow control mechanism which can exhibit incompetence either congenitally, through disease or iatrogenically due to treatment of pulmonary stenosis. A one-way valve positioned distal to the native pulmonic valve within the pulmonary artery could be of substantial benefit in overcoming this problem.

SUMMARY OF THE INVENTION

The present invention is directed to a body fluid flow control device which includes an ability to seal about the device in the fluid passageway, a placement and retention format for the device and a valve body capable of either or both a pressure threshold for operation and a one-way flow restriction. The valve body preferably end bulk resilience and a passage therethrough which is closed by that bulk resilience. This may be defined by an elastomeric or other polymeric body with a passage therethrough cut without the removal of material. A single slit, a cross or a star shaped cut are included among the possibilities. One-way flow may be accomplished through a flap or other inhibitor physically impeding flow in one direction or by a configuration of the valve to employ passage pressure to prevent opening.

In a separate aspect of the present invention, such devices as contemplated above are combined with mechanisms to assist in transforming the state of the device from insertion to anchoring.

Accordingly, it is a principal object of the present invention to provide a flow control device for the human body such as for urinary, venous or pulmonic placement. Other and further objects and advantages may appear hereinafter.

BRIEF DESCRIPTION OF THE DRAWINGS

FIG. 3 is a cross-sectional side view of a second flow control device.

FIG. 4 is an end view of a third fluid flow control device.

FIG. 5 is a cross-sectional view taken along line 5—5 of FIG. 4.

DETAILED DESCRIPTION OF THE PREFERRED EMBODIMENTS

Figure 1:
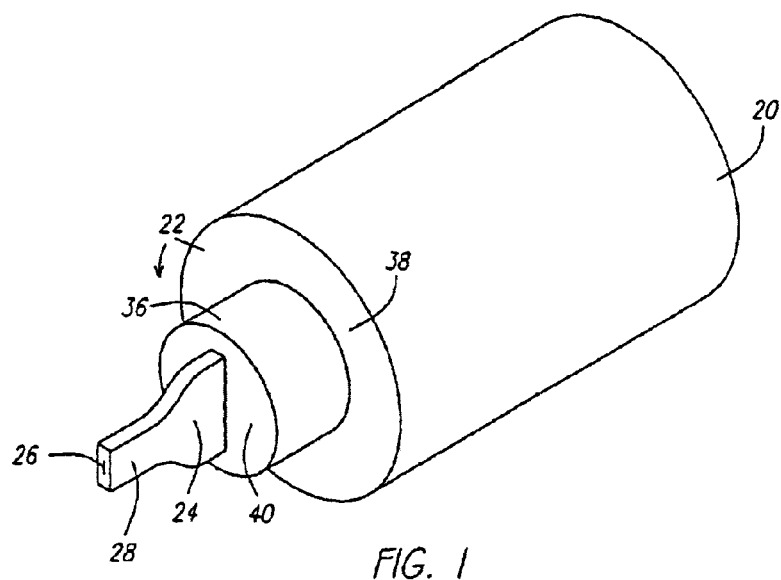
FIG. 1 is a perspective view of a first flow control device.
Figure 2:
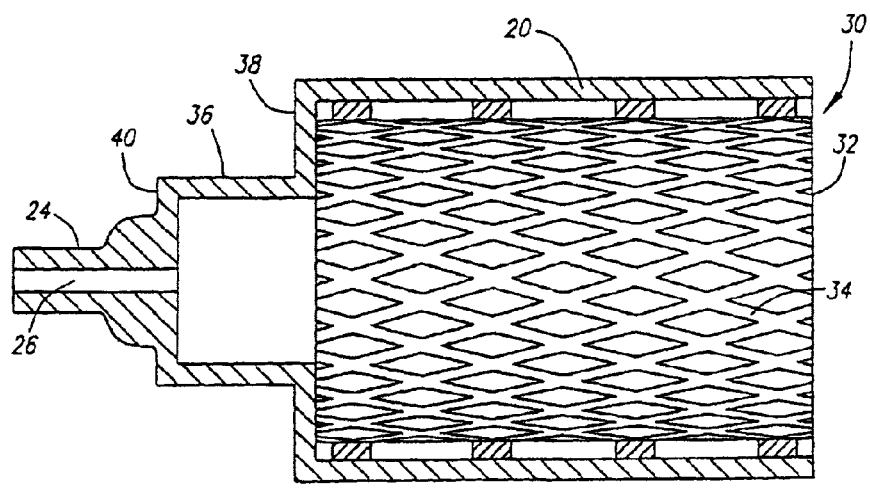
FIG. 2 is a cross-sectional side view of the device of FIG. 1.

FIGS. 1 and 2 illustrate a first fluid flow control device capable of one-way flow, the sealing of a body passageway and pressure actuation. The device includes a resilient seal 20 which, in this first embodiment, includes a cylindrical elastomeric or, more generically, polymeric material capable of sealing within the interior of a body duct or passageway. This resilient seal is shown in this embodiment to be cylindrical but may be tapered through a portion thereof. In either instance, the seal has a substantially circular cross section to fit within the body duct or passageway.

To one of the seal 20, a valve support 22 extends inwardly from an attachment to the valve body. This valve support 22 preferably provides a barrier to flow through the resilient seal. The support 22 is conveniently formed as one piece with the seal 20.

A valve body 24 is attached to the valve support 22 about the outer periphery of the body 24. The valve body 24 is also of polymeric material and may be most conveniently formed as one piece with the seal 20 and the valve support 22. The body 24 is shown in this first embodiment to define a passage 26 which is shown to be a single slit. The slit 26 extends longitudinally through the valve body. The body of the valve being polymeric and resilient is able to provide bulk resilience to maintain its natural state. As the slit 26 is preferably manufactured without removal of material form the valve body 24, the resilience of the body closes the slit 26 so that no flow can occur. Through empirical testing, an appropriate size of the slit 26 and overall body size and shape of the valve body 24 will define a threshold pressure which may be applied to one end of the valve to cause the slit 26 to open. For purposes of urinary tract control, this opening pressure should be in the range of about 0.2 psi to 3.0 psi. For intervascular placement, the threshold should be from about 0.005 psi to 1.0 psi.

The valve body 24 acts in this embodiment as a one-way valve because of the substantially parallel sides to either side of the slit 26. In the event that flow builds up on the side of the valve with the extending substantially parallel sides 28, the pressure will not only build up at the slit 26, it will also build up on the parallel sides 28 as well. The pressure on the sides will prevent the slit from opening.

A frame, generally designated 30, is located within the peripheral resilient seal 20. This frame 30 is contemplated to be a metallic member having an expanded metal cylinder 32 defined by longitudinally extending elements 34. In this instance, the longitudinally extending elements 34 are interconnected as one construction so as to form the expanded metal cylinder.

The resilient seal forming the peripheral element about the frame 30 to define a seal with the duct or passageway in which the device is placed may be affixed to the frame 30 by any number of conventional means. For example, the frame 30 may be bonded to the resilient seal 20. The resilient seal 20 may be formed through injection molding, blow molding, insertion molding or the like with the frame in place within the mold such that the frame 30 becomes embedded within the seal 20. There may be a physical interlocking through the use of an inwardly extending flange on the open end of the resilient seal 20 to physically retain the frame 30.

The frame 30, being of expanded metal, is capable of being easily stretched to expand from a stable first state to a stable expanded state. The first state, referred to as the insertion state, is contemplated with the overall diameter of the frame 30 and the surrounding resilient seal 20 exhibiting a first diameter. With the frame 30 expanded to what may be termed an anchor state, the resilient seal 20 also expands. In the expanded state, the overall device is intended to fit with interference in the duct or passage. Before expansion, easy insertion is contemplated with clearance.

The construction of this first embodiment provides for the valve support 22 to extend longitudinally in a cylindrical element 36 from an inwardly extending disk element 38. A further inwardly extending disk element 40 extends to the valve body 24. The employment of the cylindrical element 36 between these disk elements 38 and 40 is intended to isolate the valve body 24 from the displacement of the resilient seal 20 as the frame is expanded from an insertion state to an anchor state. Distortion of the valve which may result in a change in the threshold pressure to open the valve may be avoided.

Looking to FIG. 3, a similar view to that of FIG. 2 illustrates a second embodiment. This embodiment differs from the prior embodiment in the redirection of the valve body 24 at the disk 40. With that redirection, the valve body 24 is positioned to face in the opposite direction. In this way, the one-way feature operates to provide flow in the opposite direction relative to the frame 30 and resilient seal 20.

Turning to FIGS. 4 and 5, another embodiment is illustrated. Identical reference numbers are applied to those of the first embodiment to similar structures and functional elements. Presenting a more quantitative description, the wall thickness of the elastomeric polymer defining the resilient seal 20, valve support 22 and valve body 24 is contemplated to be between approximately 0.005" and 0.050". The width of the slit approximately 0.024" while the outside diameter of the resilient seal 20 is approximately 0.349". The length of this element is contemplated to be approximately 0.60". The frame is cylindrical with an OD in the insertion state of approximately 0.329", a length of approximately 0.304" and a thickness of approximately 0.005" to 0.015". This member is preferably of stainless steel or nitinol. The metallic member in this and each other embodiment is contemplated to be substantially nonreactive with body fluids and the body itself or coated with such a nonreactive material. Other dimensions can also be manufactured depending on the size of the placement.

Figures 6, 7:
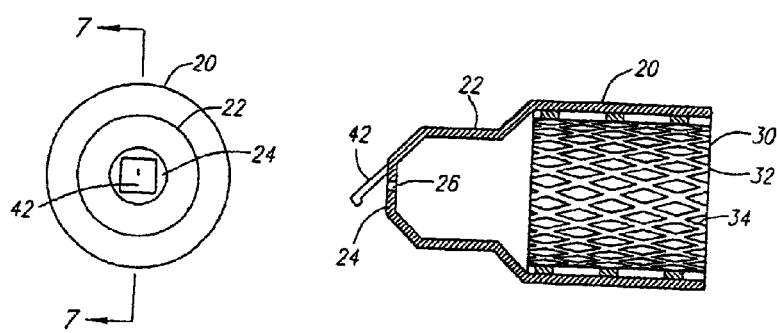
FIG. 6 is an end view of yet another fluid flow control device.
FIG. 7 is a cross-sectional view taken along line 7—7 of FIG. 6.

Turning to the embodiment of FIGS. 6 and 7, substantially the same device is illustrated as in the prior embodiment. Again, the correspondence of reference numerals reflect similar structures and functional features. This device has an added flap 42 overlying the passage 26. The flap 42 is attached by adhesive, bonding or other conventional procedure. The passage 26 may again be a slit as previously described so as to provide a threshold pressure level before opening. If a passageway is presented instead, the device will simply act as a one-way valve.

Figure 8:
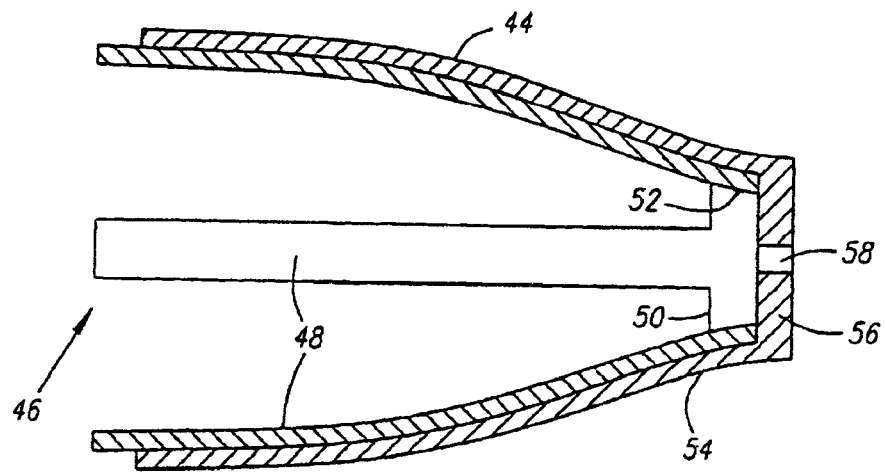
FIG. 8 is a cross-sectional view of yet another fluid flow control device.

Turning to FIG. 8, a different overall exterior configuration is presented as well as a different frame. A polymeric resilient seal 44 is shown to extend over a frame, generally designated 46. The frame 46 includes longitudinally extending elements 48. The elements 48 extend from a conically shaped portion 50 of the frame 46. This conically shaped portion 50 is truncated to provide a wide passageway 52 for operation of the valving mechanism. The resilient seal 44 forms a skirt which extends inwardly to a valve support 54 which is located about the truncated conical portion 50. The valve support 54 and the resilient seal 44 are preferably of the same piece of material. A valve body 56 extends across the passageway 52 in an appropriate thickness to provide the appropriate bulk resilience to accommodate a threshold opening pressure. A passage 58, shown here to be a slit extends through the valve body 56.

Figure 9:
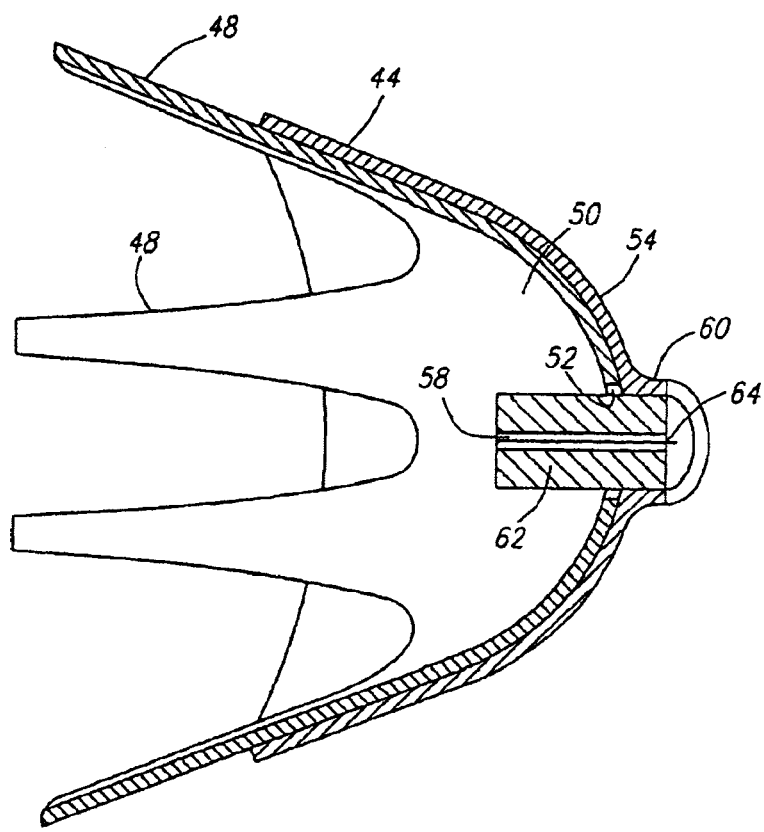
FIG. 9 is a cross-sectional view of yet another fluid flow control device.

Turning to FIG. 9, a device similar to that of FIG. 8 is disclosed. Common reference numerals indicate similar elements and functional features. The resilient seal 44 extends over the longitudinally extending elements as a skirt with the ends of the elements 48 extending outwardly therefrom. A truncated somewhat conical portion 50 actually forming a dome shape extends to a passageway 52. The valve support 54 covers this portion 50. A truncated cone shaped element 60 forms a further part of the valve. It may be part of the same piece of material as the resilient seal 44 and valve support 54. A valve body 62 is shown to be a cylindrical element with a passage 58, shown here to be slits 64 in the form of a cross or star extending longitudinally therethrough.

The length of the valve body 62 establishes that the passage 58 will operate only in expansion and not through bending of the components. Thus, a substantially greater threshold level of pressure is anticipated for this configuration.

Figure 10:
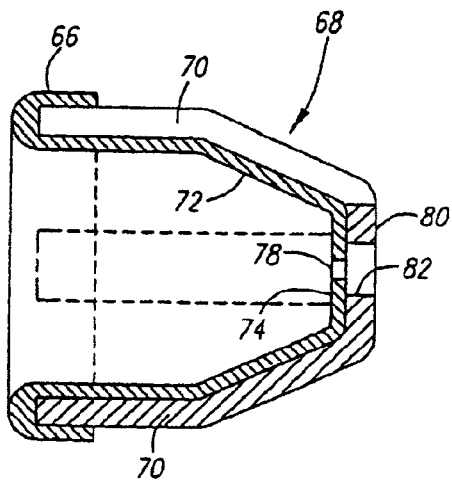
FIG. 10 is a cross-sectional view of yet another fluid flow control device.

FIG. 10 illustrates yet another fluid flow control device. This device includes a resilient seal 66 in the form of a cuff extending about one end of the periphery of the device. The frame 68 is generally on the outside of the valve with longitudinally extending elements 70 extending into the cuff 66. The valve support 72 extends with the frame 68 to a valve body 74 which forms a disk element with a slit 78 therethrough. The frame 68 includes a section in the form of a solid disk 80 with a passageway 82 therethrough. The passageway 82 is substantially larger than the slit 78 in order that it not interfere with the operation thereof. The solid disk 80 also acts to tie together the longitudinally extending element 70 extending out to the cuff 66.

A variety of slits or other mechanisms may be employed to achieve flow through a passage above a preestablished threshold pressure. With thin membranes, a slit or multiple crossed slits can employ a bending component to achieve flow. The bulk resilience is employed more in bending than in radial compression away from the cut or cuts. With longer passageways, radial compression outwardly from the passage provides the controlling mechanism. The thickness of the resilient seal as measured laterally of the slit can be of importance in one-way flow operation. With a thin lateral wall thickness, the pressure surrounding the valve can prevent its opening. Thus, flow would only occur from the side of the valve where pressure cannot accumulate and prevent its opening.

The frame is to be capable of two states, an insertion state and an anchoring state. The anchoring state is larger than the insertion state by the laterally extending resilient elements being outwardly of the insertion position of these elements when they are in the anchor state.

To achieve these two states, a number of mechanisms may be employed. First, a malleable material can be used. Because the passageways and ducts within the body are quite resilient, large changes in diameter are not required. Consequently, almost any metal is capable of sufficient malleability, particularly if it is employed in an expanded metal state, for example. Reference is made to the embodiment of FIGS. 1 and 2. The choice of metals can become more dependent upon satisfying environmental needs within the body.

Another mechanism which may be employed to accommodate this two-state requirement is spring resilience. The insertion state can be achieved through a preconstraint of the longitudinally extending elements within the elastic range of these elements. Once positioned, the elements can be released to expand into an anchoring state. Constraining tubes or pull wires may achieve the initial insertion state.

Another mechanism which may be used to accomplish both the insertion and the anchor states of the frame is the heat recovery of materials available with alloys such as certain nickel titanium alloys. Preferably the transition temperature of such devices is below body temperature. Under these circumstances, a cool device can be positioned and allowed to attain ambient temperature. The unrecovered state of the frame would be in the insertion position with the longitudinally extending elements in a radically contracted position. Upon recovery, the frame would expand. Another use of this material may be through a heating of the device above body temperature with a recovery temperature zone above that of normal body temperature but below a temperature which may cause burning. The device might be heated electrically or through the modulation of a field.

Figure 11:
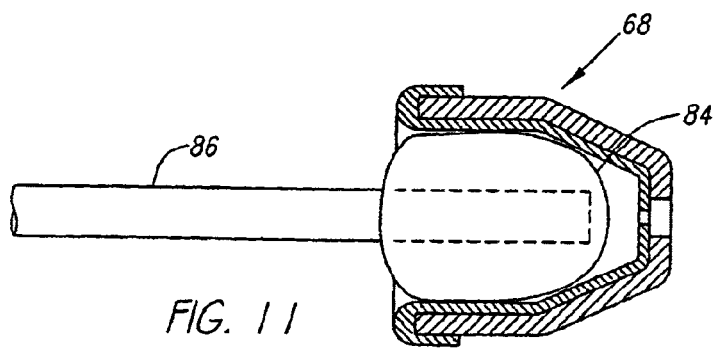
FIG. 11 is a cross-sectional view of the device of FIG. 10 with a balloon expander positioned within the device.

To accomplish a transition from the insertion state to the anchoring state, a variety of devices may be employed. An elongate expander is illustrated in FIG. 11. A balloon 84 is presented at the end of an elongate passage 86 through which pressure may be transmitted. The fluid flow control device can be inserted on the mechanism making up the passage 86 and balloon 84. When in position, the balloon 84 is expanded through the application of pressure to the accessible end of the passage 86. The malleable longitudinally extending elements are bent beyond their yield point into an interfering engagement with the wall of the passageway in the body.

Figure 12:
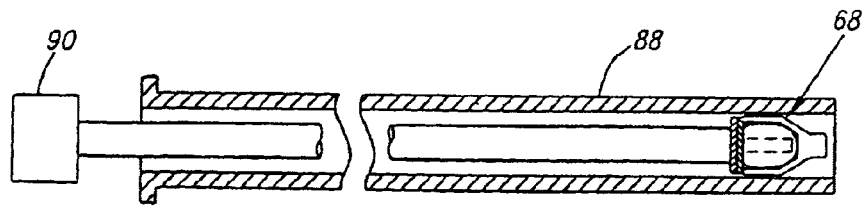
FIG. 12 is a cross-sectional side view of an insertion tool with a fluid flow control device in place.

Another mechanism for providing an elongate expander and insertion tool is illustrated in FIG. 12. The device includes an outer sheath 88 into which is positioned a fluid flow control device which has longitudinally extending elements that are of spring material. The elements are bent such that the frame is radially constricted. The size of the sheath's inner diameter is such that the spring elements are not bent to the point that they exceed the elastic limit. A ram 90 extends into the sheath 88 to force the fluid flow control device from the end of the sheath. As the device is released from the sheath 88, it will naturally expand to the anchored state. This same mechanism may be employed with any of the devices for placement regardless of whether the mechanism for expansion is deformation, heat recovery or resilience. Naturally, the ram 90 can accommodate a heating element or balloon mechanism depending upon the appropriate need.

Figure 13:
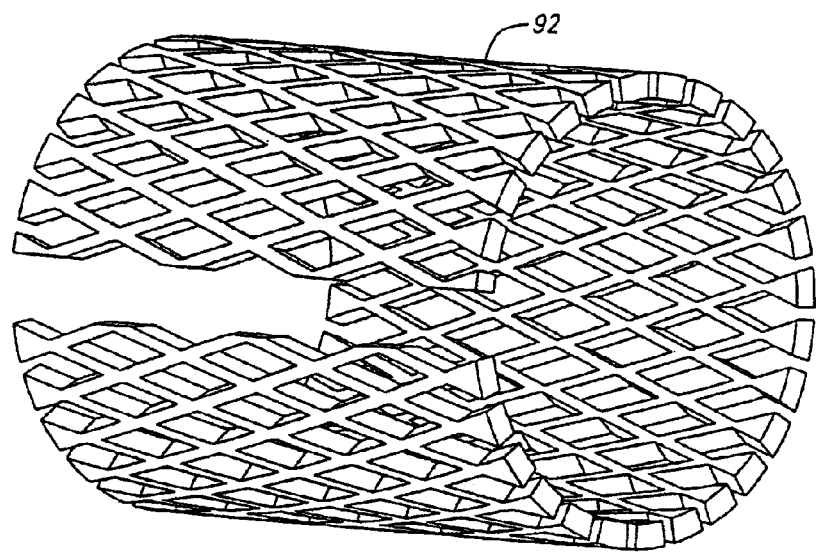
FIG. 13 is a prospective view of another frame.
Figure 14:
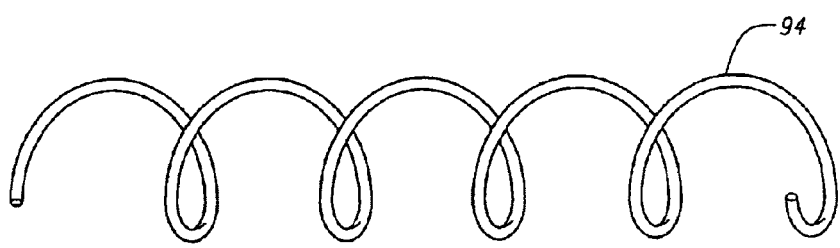
FIG. 14 is a prospective view of yet another frame.

Finally, FIGS. 13 and 14 illustrate two additional forms of the frame which may be employed in place of one of the other frames disclosed. The frame may form a complete cylinder or a rolled sheet 92 as in FIG. 13. A frame which is another alternative is seen in FIG. 14. A longitudinally extending element 94 is formed into a coil. These devices may be of heat recoverable material so as to form an insertion state and an anchor state or be of spring material constrained to a reduced diameter for insertion.

Considering the use of these devices, the thresholds are selected with the appropriate pressures in mind. With incontinence, the threshold pressure is high enough to prevent leakage as normal pressure builds in the bladder. When the bladder is to be voided, abdominal pressure is used. The threshold pressure is also low enough that the abdominal pressure will overcome the resistance and allow flow. Where placement is in the cardiovascular system, minimum resistance to flow in one direction may be designed into the valve. In this application, however, substantial resistance to flow is designed into the valve to eliminate flow in one direction for all pressures contemplated.

Accordingly, a number of improved devices for providing body fluid flow control are disclosed. While embodiments and applications of this invention have been shown and described, it would be apparent to those skilled in the art that may more modifications are possible without departing from the inventive concepts herein. The invention, therefore is not to be restricted except in the spirit of the appended claims.

What is claimed is:

1. A body fluid flow control device for placement in a body lumen comprising:
   a valve body having a passage and a first portion movable between an open configuration allowing fluid flow through the passage and a closed configuration restricting fluid flow through the passage, the first portion being biased into the closed configuration and movable into the open configuration in response to fluid flow;
   an annular seal having a collapsed configuration suitable for insertion into the body lumen and an expanded configuration adapted to seal with a wall of the body lumen, wherein the seal is cylindrical; and
   a valve support coupled to the valve body and to the seal, the valve support isolating the valve body from the seal to avoid distortion of the valve body when the seal is in the expanded configuration.

2. The body fluid flow control device of claim 1, further comprising a frame coupled to the seal and including a passageway extending longitudinally through the frame in communication with the passage in the valve body, the frame being movable between an insertion state and an anchoring state, the anchoring state having a transverse dimension larger than the insertion state, the seal being movable with the frame to seal with the wall of the body lumen in the anchoring state.

3. The body fluid control device of claim 2, wherein the valve body has a first outer diameter and the frame has a second outer diameter, the first outer diameter being less than the second outer diameter.

4. The body fluid control device of claim 2 wherein the valve body is axially displaced from the frame.

5. The body fluid control device of claim 2, wherein the valve body is outside the passageway in the frame.

6. The body fluid control device of claim 2, wherein the seal is disposed on an outer surface of the frame such that the seal is disposed between the frame and the wall of the body lumen in the anchoring state.

7. The body fluid control device of claim 2, wherein the frame compresses the seal against the wall of the body lumen in the anchoring state.

8. The body fluid flow control device of claim 2, wherein the frame is embedded within at least a portion of the seal.

9. The body fluid flow control device of claim 1, wherein the first portion of the valve body moves from the closed configuration to the open configuration at a threshold pressure, the valve support being adapted to maintain the threshold pressure generally constant during displacement of the seal.

10. The body fluid control device of claim 1, wherein the valve support is an elastomeric material.

11. The body fluid control device of claim 1, wherein the valve support is integrally formed with the valve body.

12. The body fluid control device of claim 1, wherein the valve support is integrally formed with the seal.

13. The body fluid control device of claim 1, wherein the valve support is disposed circumferentially around the valve body.

14. The body fluid control device of claim 1, wherein the valve body has an outer diameter less than an inner diameter of the seal, the valve support comprising an annular member between the valve body and the seal.

15. The body fluid control device of claim 1, wherein the valve body comprises a pair of walls separated by a slit, the walls being substantially parallel.

16. The body fluid flow control device of claim 1, wherein the valve support isolates the valve body from the seal to avoid distortion of the valve body as the seal moves between the collapsed configuration and the expanded configuration.

17. A body fluid flow control device for placement in a body lumen comprising:

a valve body having a passage and a first portion movable between an open configuration allowing fluid flow through the passage and a closed configuration restricting fluid flow through the passage, the first portion being biased into the closed configuration and movable into the open configuration in response to fluid flow;

an annular seal adapted to seal with a wall of the body lumen, wherein the seal is cylindrical;

a frame coupled to the seal and including a passageway extending longitudinally through the frame in communication with the passage in the valve body, the frame being movable between an insertion state and an anchoring state, the anchoring state having a transverse dimension larger than the insertion state, the seal being movable with the frame to seal with the wall of the body lumen in the anchoring state; and a valve support coupled to the valve body and to the seal, the valve support isolating the valve body from the seal to avoid distortion of the valve body when the frame is in the anchoring state.

18. The body fluid flow control device of claim 17, wherein the valve support isolates the valve body from the seal to avoid distortion of the valve body as the frame moves between the insertion state and the anchoring state.

* * * * *

UNITED STATES PATENT AND TRADEMARK OFFICE
CERTIFICATE OF CORRECTION

| | | |
|---|---|---|
| PATENT NO. | : 7,033,387 B2 | |
| APPLICATION NO. | : 10/419653 | |
| DATED | : April 25, 2006 | |
| INVENTOR(S) | : Zadno-Azizi et al. | |

It is certified that error appears in the above-identified patent and that said Letters Patent is hereby corrected as shown below:

IN THE TITLE PAGES:
In Item [57] ABSTRACT, at line 9, please replace "elongate" with --elongated--

In Item [56] References Cited, U.S. PATENT DOCUMENTS:
    please add the following reference:
        --5,522,881 A 6/1996 Lentz 623/1.13--
    in 6,485,407 please replace "B1" with --B2--
    in 6,527,761 please replace "Buch et al." with --Soltesz et al.--

In Item [56] References Cited, OTHER PUBLICATIONS:
    in Article:, following "Development" please insert
        --available at <http://www.kulisz.com/autocath.htm>,
        last accessed Jul. 9, 2002--
    in Woodring et al., please insert --ex-- between "Pneumothorax" and "Vacuo",
        and replace "100" with --110--, and replace "1124" with --1105--

UNITED STATES PATENT AND TRADEMARK OFFICE
CERTIFICATE OF CORRECTION

PATENT NO.        : 7,033,387 B2
APPLICATION NO.   : 10/419653
DATED             : April 25, 2006
INVENTOR(S)       : Zadno-Azizi et al.

Page 2 of 2

It is certified that error appears in the above-identified patent and that said Letters Patent is hereby corrected as shown below:

IN THE DRAWINGS:
In Drawing Sheet 1, please replace Figure 1 with the following figure:

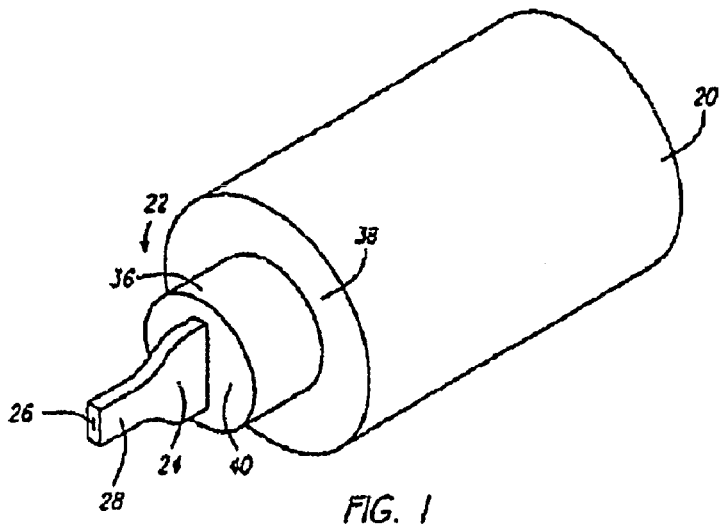

FIG. 1

IN THE SPECIFICATION:
At column 5, line 16, please replace "outwardly" with --outward--

Signed and Sealed this

Twenty-eighth Day of November, 2006

JON W. DUDAS
*Director of the United States Patent and Trademark Office*